US00PP35771P2

(12) United States Plant Patent
Hattori

(10) Patent No.: US PP35,771 P2
(45) Date of Patent: Apr. 23, 2024

(54) ***HELLEBORUS* PLANT NAMED 'TABLE MOUNTAIN'**

(50) Latin Name: ***Helleborus argutifolius* X *Helleborus lividus***
Varietal Denomination: Table Mountain

(71) Applicant: Miyoko Hattori, Tokyo (JP)

(72) Inventor: Miyoko Hattori, Tokyo (JP)

( * ) Notice: Subject to any disclaimer, the term of this patent is extended or adjusted under 35 U.S.C. 154(b) by 0 days.

(21) Appl. No.: 18/235,839

(22) Filed: Aug. 19, 2023

(51) Int. Cl.
*A01H 5/02* (2018.01)
*A01H 6/72* (2018.01)

(52) U.S. Cl.
USPC ..... Plt./439
CPC ..... *A01H 6/72* (2018.05)

(58) Field of Classification Search
USPC ..... Plt./439
CPC ..... A01H 6/72; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Helleborus* plant named 'Table Mountain', characterized by its relatively compact, upright to outwardly spreading and mounding plant habit; moderately vigorous growth habit; leaflets that have green-colored upper surfaces and dark red-colored lower surfaces that become goldish green in color with subsequent development; freely flowering habit; dark red-colored flowers that are held within the foliar plane that fade to a dusty rose with green-colored accents with subsequent development; and good garden performance.

2 Drawing Sheets

Figure 1:
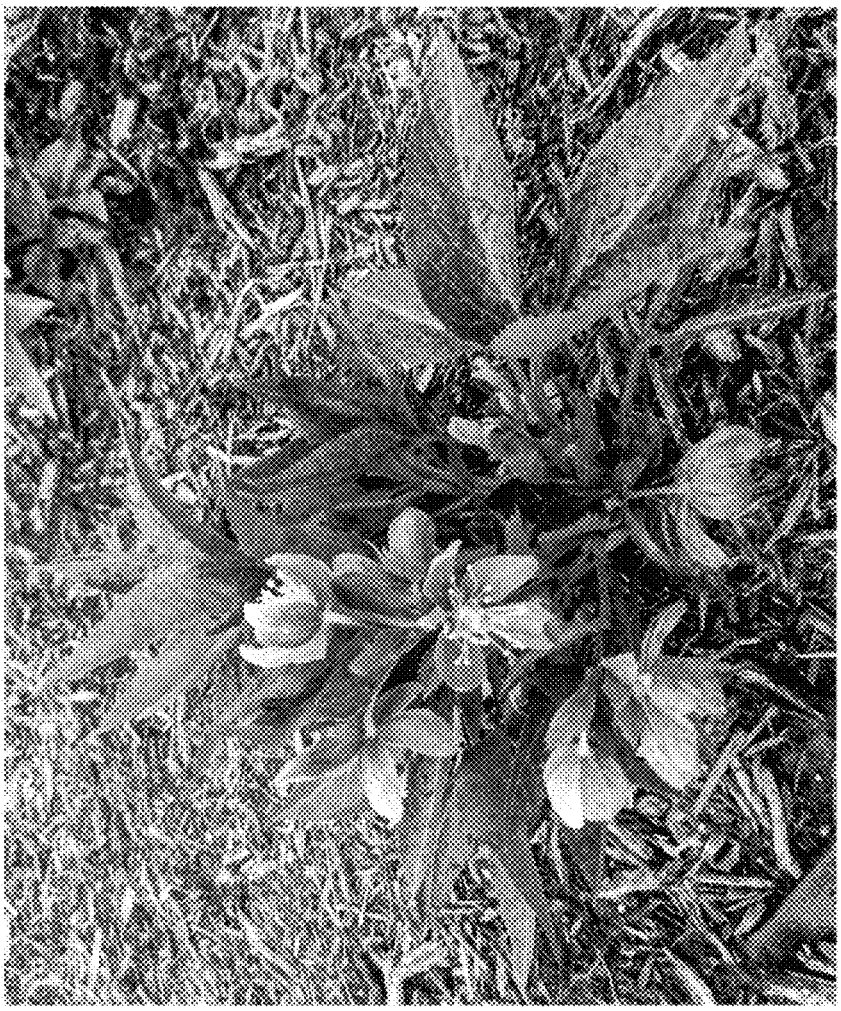

Botanical designation: *Helleborus argutifolius* X *Helleborus lividus*.

Cultivar denomination: 'TABLE MOUNTAIN'.

BACKGROUND OF THE INVENTION

The present invention relates to a new and distinct cultivar of *Helleborus* plant, botanically known as *Helleborus argutifolius* X *Helleborus lividus* and hereinafter referred to by the name 'Table Mountain'.

The new *Helleborus* plant is a product of a planned breeding program conducted by the Inventor in Tokyo, Japan. The objective of the breeding program was to create new vigorous and freely-flowering *Helleborus* plants with attractive leaves and flowers.

The new *Helleborus* plant originated from a cross-pollination conducted by the Inventor in Toyko, Japan in March, 2016 of a proprietary selection of *Helleborus argutifolius* identified as code "A", as the female, or seed, parent, not patented, with a proprietary selection of *Helleborus lividus* identified as code "A" as the male, or pollen, parent, not patented. The new *Helleborus* plant was discovered and selected by the Inventor as a single flowering plant from within the progeny of the stated cross-pollination grown in a controlled greenhouse environment in Tokyo, Japan in March, 2018.

Asexual reproduction of the new *Helleborus* plant by divisions in a controlled greenhouse environment in Tokyo, Japan since March, 2018, has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype of the new *Helleborus* plant may vary somewhat with variations in environmental conditions such as temperature and light intensity without, however, any variance in genotype of the new *Helleborus* plant.

The following traits have been repeatedly observed and are determined to be the unique characteristics of 'Table Mountain'. These characteristics in combination distinguish 'Table Mountain' as a new and distinct *Helleborus* plant:

1. Relatively compact, upright to outwardly spreading and mounding plant habit.
2. Moderately vigorous growth habit.
3. Leaflets that have green-colored upper surfaces and dark red-colored lower surfaces that become goldish green in color with subsequent development.
4. Freely flowering habit.
5. Dark red-colored flowers that are held within the foliar plane that fade to a dusty rose with green-colored accents with subsequent development.
6. Good garden performance.

Plants of the new *Helleborus* differ primarily from plants of the female parent selection in leaflet color as leaflets of plants of the new *Helleborus* become goldish green in color with subsequent development whereas leaflets of plants of the female parent selection do not become goldish green in color. In addition, plants of the new *Helleborus* are more compact than plants of female parent selection.

Plants of the new *Helleborus* differ primarily from plants of the male parent selection in leaflet margins as leaflets of plants of the new *Helleborus* have deep serrations whereas leaflets of plants of the male parent do not have deep serrations.

Plants of the new *Helleborus* can be compared to plants of *Helleborus niger* X *Helleborus lividus* 'COSEH 700', disclosed in U.S. Plant Pat. No. 21,003. In side-by-side comparisons, plants of the new *Helleborus* differ from plants of 'COSEH 700' in the following characteristics:

1. Plants of the new *Helleborus* are larger than plants of 'COSEH 700'.
2. Plants of the new *Helleborus* have longer leaflets than plants of 'COSEH 700'.
3. Leaflets of plants of the new *Helleborus* are lighter green in color and become goldish green in color with subsequent development whereas leaflets of plants of 'COSEH 700' are darker green in color and do not become goldish green in color with subsequent development.
4. Petioles of plants of the new *Helleborus* are dark red in color whereas petioles of plants of 'COSEH 700' are dark greyish reddish brown in color.
5. Plants of the new *Helleborus* are not as freely flowering as plants of 'COSEH 700'.
6. Flowers of plants of the new *Helleborus* are dark red in color whereas flowers of plants of 'COSEH 700' are light yellow green in color.
7. Plants of the new *Helleborus* have shorter peduncles than plants of 'COSEH 700'.
8. Flowers of plants of the new *Helleborus* have fewer stamens than plants of 'COSEH 700'.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet (FIG. 1) is a side perspective view of a typical flowering plant of 'Table Mountain' grown in an outdoor nursery.

Figure 2:
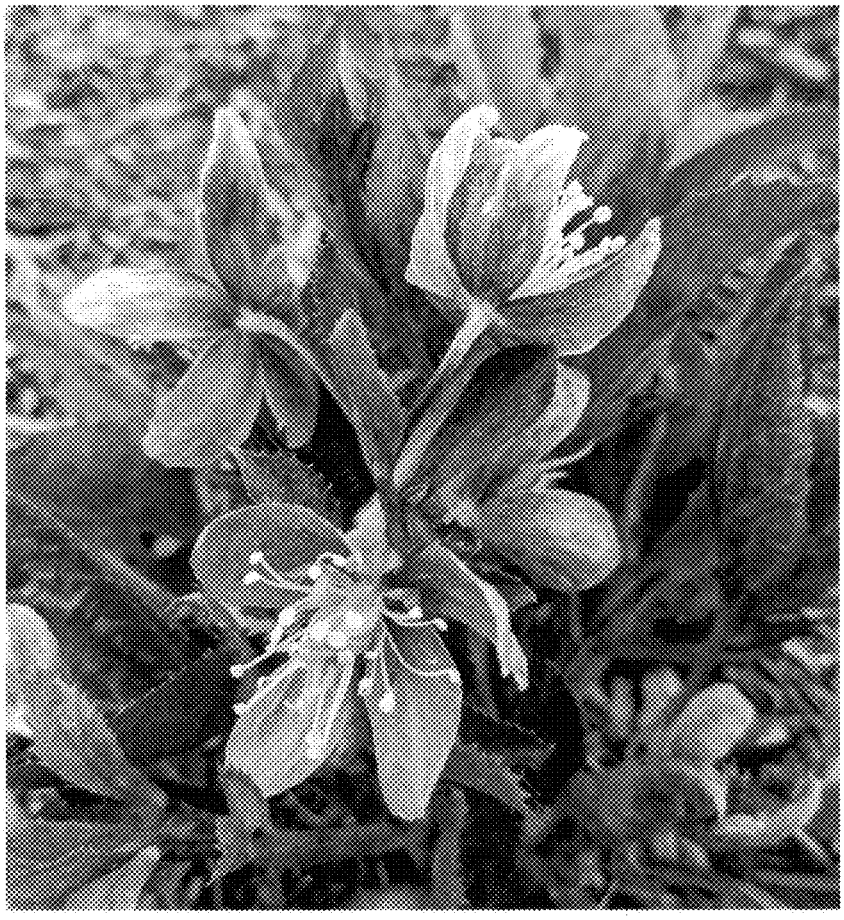

The photograph on the second sheet (FIG. 2) is a close-up view of typical flowers of 'Table Mountain'.

DETAILED BOTANICAL DESCRIPTION

The aforementioned photographs and following observations, measurements and values describe plants grown during the spring in an outdoor nursery in Smoketown, Pennsylvania and under cultural practices typical of commercial *Helleborus* production. During the production of the plants, day temperatures averaged 23 C, night temperatures averaged 12 C and light levels averaged 11.43 Klux. Plants were 1.75 years old when the photograph and the description were taken. In the following description, color references are made to The Royal Horticultural Society Colour Chart, Sixth Edition, except where general terms of ordinary dictionary significance are used.

Botanical classification: *Helleborus argutifolius* X *Helleborus lividus* 'Table Mountain'.

Parentage:

*Female, or seed, parent.*—*Helleborus argutifolius* identified as code "A", not patented.

*Male, or pollen, parent.*—Proprietary selection of *Helleborus lividus* identified as code "A", not patented.

Propagation:

*Type.*—By meristem culture.

*Time to initiate roots.*—About three to four weeks at soil temperatures about 21 C to 22 C.

*Time to produce a rooted young plant.*—About six to eight weeks at soil temperatures about 21 C to 22 C.

*Root description.*—Fleshy, medium in thickness; typically brown to white in color, actual color of the roots is dependent on substrate composition, water quality, fertilizer type and formulation, substrate temperature and physiological age of roots.

*Rooting habit.*—Moderate branching; medium density.

Plant description:

*Plant and growth habit.*—Herbaceous perennial; relatively compact, upright to outwardly spreading and mounding plant habit; moderately vigorous growth habit and moderate growth rate; leaves arranged in basal rosettes.

*Plant height, soil level to top of foliar plane.*—About 30 cm.

*Plant height, soil level to top of floral plane.*—About 18 cm.

*Plant diameter* (*area of spread*).—About 40 cm.

Leaf description:

*Arrangement.*—Leaves arranged alternately in a basal rosette; leaves palmately compound with typically three leaflets per leaf.

*Leaflet length.*—About 12 cm to 14 cm.

*Leaflet width.*—About 4 cm to 5 cm.

*Leaflet shape.*—Elliptic.

*Leaflet apex.*—Acute.

*Leaflet base.*—Acute to oblique.

*Leaflet margin.*—Serrate.

*Leaflet texture and luster, upper surface.*—Smooth, glabrous; leathery; somewhat glossy.

*Leaflet texture and luster, lower surface.*—Smooth, glabrous; leathery; matte and waxy.

*Leaflet venation pattern.*—Pinnate and reticulate.

*Leaflet color.*—Developing leaflets, upper surface: Close to 144A. Developing leaflets, lower surface: Close to 187A. Fully expanded leaflets, upper surface: Close to 144A; color becoming closer to 153D with subsequent development; venation, close to 187B. Fully expanded leaflets, lower surface: Close to 187A with waxy overlay; venation, close to 187A.

*Petioles.*—Length, fully expanded leaflets: About 9 cm to 11 cm. Diameter, fully expanded leaflets: About 3 mm to 8 mm. Strength: Moderately strong. Texture and luster, upper and lower surfaces: Smooth, glabrous; moderately glossy and waxy. Color, upper surface: Close to 187A lightly speckled with close to 145C. Color, lower surface: Close to 187A speckled with close to 145C; at the apex, close to 145C.

Flower description:

*Flower shape and habit.*—Single rotate cyanthiform flowers arranged in terminal and axillary cymes; freely flowering habit with typically about 12 to 15 flowers developing per plant; flowers face outwardly to slightly upright.

*Fragrance.*—Slightly fragrant, pleasant.

*Natural flowering season.*—Plants flower in April and May in Pennsylvania.

*Flower longevity on the plant.*—About two weeks; sepals are persistent and other flower parts are not persistent.

*Flower buds.*—Length: About 2 cm. Diameter: About 2 cm. Shape: Orbicular. Texture and luster: Smooth, glabrous; matte. Color: Close to N186C.

*Inflorescence height.*—About 18 cm.

*Inflorescence diameter*.—About 15 cm.

*Flower diameter*.—About 4 cm.

*Flower depth* (*height*).—About 3 cm.

*Petals*.—None observed; transformed into nectaries.

*Sepals*.—Quantity and arrangement: About five arranged in a single whorl. Length: About 2.5 cm. Width: About 1.5 cm. Shape: Broadly ovate; concave. Apex: Obtuse, rounded. Base: Acute. Margin: Mostly entire to finely serrate. Texture and luster, upper and lower surfaces: Smooth, glabrous; leathery; matte. Color: When opening, upper surface: Proximally, close to 59A and distally, close to 142C. When opening, lower surface: Close to 187A. Fully opened, upper surface: Close to 183A to 183B and at the center and apex, close to 145B to 145C; with subsequent development, color becomes closer to 182B to 182C and at the center and apex, close to 145B to 145C. Fully opened, lower surface: Close to 187A; with subsequent development, color becomes closer to 182B to 182C and at the center and apex, close to 145B to 145C.

*Flower bracts*.—Quantity and arrangement: About two at the base of the flower. Length: About 3 cm. Width: About 1 cm. Shape: Narrowly elliptic to somewhat linear. Apex: Acute. Base: Attenuate. Margin: Serrate. Texture and luster, upper and lower surfaces: Smooth, glaucous; leathery; matte. Color: When opening and fully opened, upper surface: Proximally, close to N77A and distally, close to 143A to 143B. When opening and fully opened, lower surface: Close to N77A.

*Peduncles*.—Length: About 5 cm. Diameter: About 3 mm. Strength: Strong. Aspect: About 10 to 25 degrees from plant axis. Texture and luster: Smooth, glabrous; matte and waxy. Color: Close to N77A lightly speckled with close to 145B.

*Reproductive organs*.—Stamens: Quantity per flower: About 18. Filament length: About 1.2 cm to 1.5 cm. Filament color: Close to 1A. Anther shape: Oblong and retuse. Anther size: About 1 mm by 2 mm. Anther color: Close to 5A. Pollen amount: None observed. Pistils: Quantity per flower: About five to seven. Pistil length: About 1.5 cm to 2 cm. Stigma shape: Tapered, pointed. Stigma color: Close to 145A. Style length: About 1.5 cm to 2 cm. Style color: Close to 145A. Ovary color: Close to 150C.

*Nectaries*.—Quantity per flower: About eight. Length: About 1 cm. Width: Close to 1 mm. Shape: Tubular. Apex: Slanted. Margin: Entire; slightly undulate. Texture and luster: Smooth, glaucous; matte. Color: Close to N144A and towards the apex, close to 1A.

*Seeds and fruits*.—To date, seed and fruit development have not been observed on plants of the new *Helleborus*.

Garden performance: Plants of the new *Helleborus* have been observed to have good garden performance and to tolerate rain, wind and temperatures ranging from about −15 C to about 34 C.

Pathogen & pest resistance: To date, plants of the new *Helleborus* have not been observed to be resistant to pathogens and pests common to *Helleborus* plants.

It is claimed:

1. A new and distinct *Helleborus* plant named 'Table Mountain' as illustrated and described.

* * * * *